United States Patent [19]

Gold et al.

[11] Patent Number: 4,658,060

[45] Date of Patent: Apr. 14, 1987

[54] PREPARATION OF (−)-5-(BETA)-1-HYDROXY-2-((BETA)-1-METHYL-3-PHENYLPROPYL)AMINO-ETHYL) SALICYLAMIDE

[75] Inventors: Elijah J. Gold; Esther Babad; Lydia Peer, all of West Orange; Wei K. Chang, Livingston, all of N.J.

[73] Assignee: Schering Corporation, Kenilworth, N.J.

[21] Appl. No.: 371,622

[22] Filed: Apr. 26, 1982

[51] Int. Cl.$^4$ .......................................... C07C 103/29
[52] U.S. Cl. .............................. 564/165; 260/561.18; 564/304
[58] Field of Search .................. 564/165, 304, 381

[56] References Cited

U.S. PATENT DOCUMENTS

| | | | |
|---|---|---|---|
| 4,000,197 | 12/1976 | Barfknecht et al. | 564/381 |
| 4,012,444 | 3/1977 | Lunts et al. | 564/165 |
| 4,101,579 | 7/1978 | Hartley et al. | 564/165 |
| 4,137,328 | 1/1979 | Cox et al. | 564/165 X |
| 4,173,583 | 11/1979 | Gold et al. | 564/165 X |

*Primary Examiner*—Robert V. Hines
*Attorney, Agent, or Firm*—Anita W. Magatti; Gerald S. Rosen

[57] ABSTRACT

There is disclosed a multistep process for producing (−)-5-[(R)-1-hydroxy-2-((R)-1-methyl-3-phenyl-propyl)aminoethyl]salicylamide in high yields which does not require chromatography.

The process is stereoselective for the desired products starting with the reaction of D-(+)-alpha-methylben-zylamine with benzylacetone followed by reduction of the resulting Schiff's base to form an amine as an R,R: R,S diastereomeric mixture, resolution of the mixture to obtain the R,R stereoisomer as a salt, conversion to a free base, reaction of the R,R free base with an O-protected alpha-bromo-3-carbamoyl-acetophenone to produce the corresponding R,R-ketobenzamide, reduction to produce a mixture of S,R,R;R,R,R hydroxyben-zamide, removal of the protecting groups, resolution of the deprotected product and then conversion to the free R,R-amine.

7 Claims, No Drawings

PREPARATION OF (−)-5-(BETA)-1-HYDROXY-2-((BETA)-1-METHYL-3-PHENYLPROPYL)AMINOETHYL) SALICYLAMIDE

BACKGROUND

5-[1-hydroxy-2-(1-methyl-3-phenylpropyl)aminoethyl]salicylamide a substance known as labetalol is a well known antihypertensive agent as disclosed in U.S. Pat. No. 4,012,444. Labetalol is a mixture of all four possible optically active stereoisomers which can be designated R,R; R,S; S,R; and S,S according to the Cahn-Ingold, Prelog system. (−)-5-[(R)-1-hydroxy-2-((R)-1-methyl-3-phenylpropyl)aminoethyl]salicylamide, hereafter for convenience refered to as the R,R stereoisomer is of interest. It possesses unique properties compared with the other isomeric forms, and labetalol, enabling it to be used in the treatment of hypertension as discussed in detail in European Patent No. 79103473.9 Publication No. 9702. incorporated by reference herein. The R,R stereoisomer substantially free of the other stereoismers can be prepared by a series of process steps requiring chromatographic operations on diastereomeric intermediates in order to ensure the desired sterically pure final product is obtained.

Thus European Patent Application No. 79103473.9 Publication No. 9702 describes the stereoselective synthesis of the HCl acid addition salt of the R,R stereoisomer by a procedure involving the chromatographic separation of the desired isomer from a diastereomeric mixture.

We have now found that by employing certain stereospecific intermediates the R,R stereoisomer may conveniently be prepared by a process involving resolution of intermediates by salt formation instead of by chromatography.

SUMMARY

The present invention provides a method for the production of the R,R stereoisomer which does not require chromatography and which in its preferred form, results in high yields.

The process of this invention is a novel multi-step process in which certain individual steps are novel and in which certain of the intermediates are novel.

In essence we have found that proceeding with synthesis of the R,R stereoisomer via reduction of the precursor 2-(O-protected)-5-[(R)-α-methylbenzyl]-N-[(R)-1-methyl-3-phenylpropyl)glycyl]benzamide, affords more of the stereoisomeric intermediate with the desired R configuration at the newly formed hydroxyl chiral center than heretofore possible. Subsequent removal of the protecting groups yields a mixture consisting mainly of the desired R,R stereoisomer and a very minor amount of its S,R diastereomer. This mixture is readily resolved by salt formation to afford the desired compound. There is no need in the process of this invention for chromatographic separation of any intermediates.

The above precursor itself can be formed from two intermediates, one of which is an optically active compound. This optically active compound is readily obtainable from a diastereomeric mixture (in which it is the major product) by non-chromatographic resolution.

Thus, the present invention provides a method for the preparation of (−)-5-[(R)-1-hydroxy-2-((R)-1-1-methyl-3-phenyl-propyl)aminoethyl]salicylamide.

DETAILED DESCRIPTION OF THE INVENTION

In a preferred embodiment described below the R,R stereoisomer of labetalol is produced by following the reaction sequence shown below:

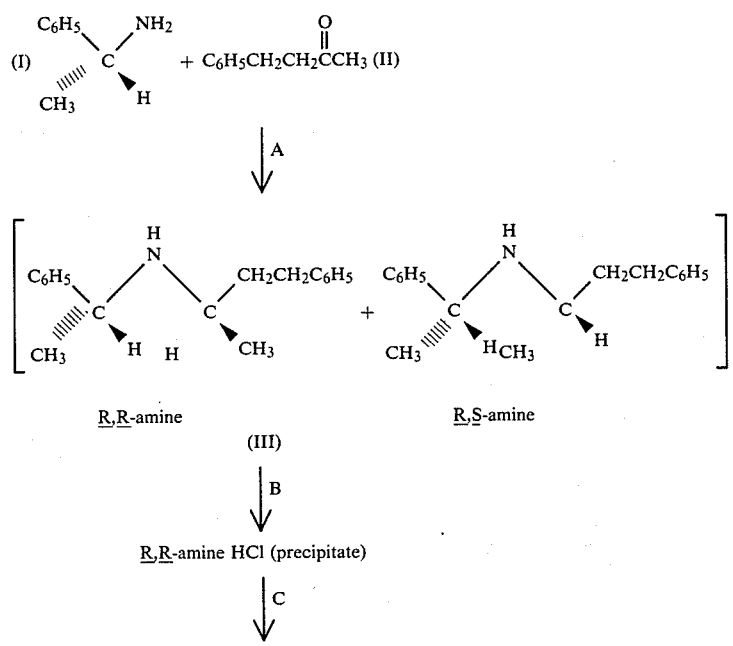

-continued
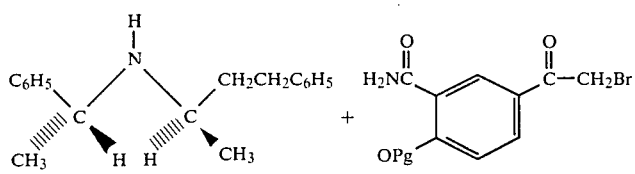
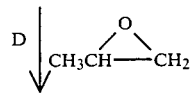
Pg = hydroxy protecting group
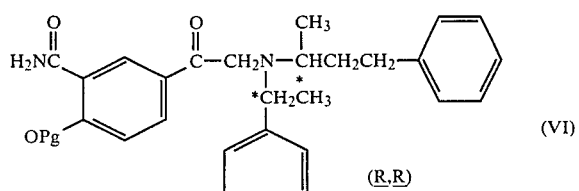
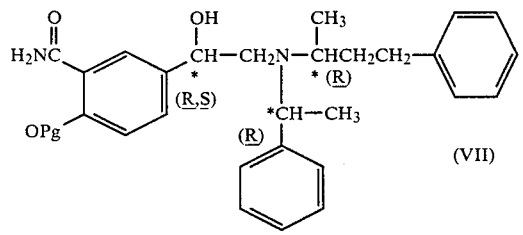
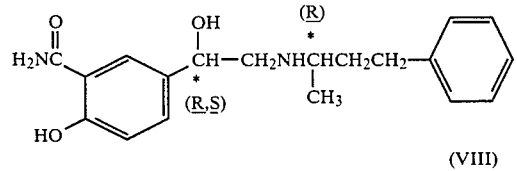
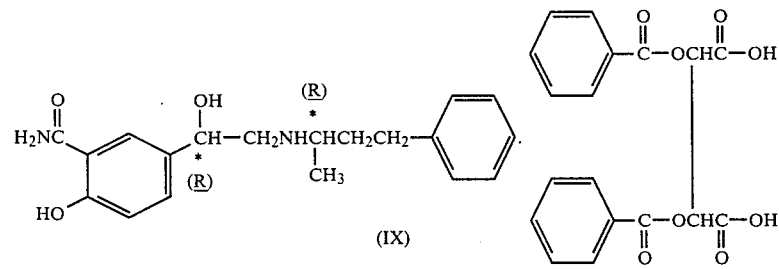

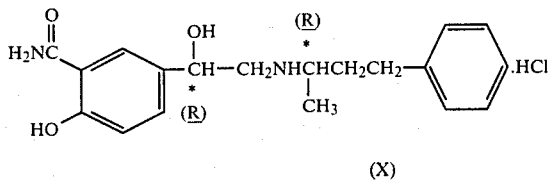

(X)

STEP A

D-(+)-α-methylbenzylamine is reacted with benzylacetone and the resulting Schiff's base is reduced to form amines (III). Conveniently the reaction is carried out under reducing conditions so that isolation of a Schiff's base intermediate is unnecessary. Reducing conditions are suitably provided by hydrogenating in the presence of Raney Nickel. Usually the reaction will be carried out in an organic solvent inert towards the reactants for example isopropanol. In an embodiment described below, after reduction, a diastereomeric mixture (R,R and R,S) of about 3 parts by weight of the desired N-[(R)-α-methylbenzyl]-(R)-1-methyl-3-phenyl-propylamine (i.e. the R,R stereoisomer) is produced.

STEP A¹

N-((R)-α-methylbenzyl)-R,S)-1-methyl-3-phenylpropylamine may also be prepared by first forming a Schiff's base in one operation; and thereafter reducing the Schiff's base in a second distinct operation. The same starting materials can be used as in Step A. In one operation a Schiff's base is formed by condensing D-(+)-α-methylbenzylamine with benzylacetone in a solvent mixture of toluene or xylene and toluene sulfonic acid with azeotropic removal of the water formed in the reaction. After removal of the solvent the crude imine is dissolved in a suitable solvent e.g. glacial acetic acid and reduced using Raney Nickel. Distillation of the product to yield (R,R; R,S) mixture.

STEP B

The diastereomeric mixture from Step A or A¹ can be readily resolved by formation of an acid addition salt by conventional methods. For instance the HCl acid addition salt of the R,R stereoisomer can be selectively precipitated from a solution of the diastereomeric mixture in an organic solvent by bubbling HCl therethrough or preferably by adding thereto a solution of HCl gas in isopropanol.

STEP C

The R,R amine HCl salt resulting from Step B can be converted to the free base by conventional methods, for instance by reaction with an aqueous NaOH solution, in e.g. an organic solvent for instance toluene, usually under an inert atmosphere e.g. nitrogen, followed by working up in a conventional manner.

STEP D

The free base R,R amine from Step C is reacted with a 4-O-protected-α-bromo-3-carbamoyl-acetophenone to produce a 2-(O-protected)-5[((R)-α-methylbenzyl-N-(R)-1-methyl-3-phenylpropyl)glycyl]benzamide (VI). The reaction is carried out in the presence of a nonbasic acid acceptor which is preferably propylene oxide. The reaction is conveniently carried out under reflux conditions in an inert organic solvent for example dimethylformamide. It is desirable, for best results, to conduct the reaction and subsequent work-up in the absence of light. The protecting group Pg is suitably any readily removable conventional hydroxy protecting group and is preferably benzyl.

STEP E

The keto group of compound VI resulting from Step D is subjected to reduction, ideally under mild conditions which do not affect the protecting group Pg or the α-methyl benzyl group attached to the nitrogen atom and to which it performs a protective function, to produce a diastereomeric mixture 2-(phenylmethoxy)-5-[(R,S)-1-hydroxy-2-[((R)-1-methyl-3-phenylpropyl)-(R)-α-methylbenzylamine]ethyl]benzamide (VII). Generally speaking, suitable reducing conditions will be well known to persons skilled in the art. One convenient procedure is to reduce with sodium borohydride or sodium cyanoborohydride, the reaction being conducted in an organic solvent, e.g. ethanol.

STEP F

The product VII of Step E is an isomeric mixture (R,R,R and S,R,R) of about 9 parts by weight of the desired R,R,R isomer. It is treated to affect removal of the hydroxy protecting group Pg and N-protecting α-methyl benzyl group to afford the product as a diastereomeric mixture, 5-[(R,S)-1-hydroxy-2-[(R)-1-methyl-3-phenylpropylamino]ethyl]salicylamide (VIII). Suitable conditions will be known to the skilled man in the art. We prefer to operate by hydrogenation in the presence of a palladium on carbon catalyst.

Resolution of the deprotected product VIII from Step F is usually carried out by treating it in an organic solvent, e.g. ethanol, with a suitable resolving agent such as dibenzoyl-d-tartaric acid monohydrate and allowing crystals to form, usually at room temperature. The first crop of crystals is the desired R,R isomer of labetalol in the form of its salt, e.g. the dibenzoyl-d-tartrate acid salt. It is usually desirable to seed the starting solution with a previously prepared R,R isomer dibenzoyl-d-tartaric acid salt.

The HCl acid addition salt can be formed by the conventional technique of adding a solution by HCl gas in an organic solvent e.g. ethanol to a solution in slurry of the acid addition salt obtained from Step F. After allowing the reaction to proceed for a suitable period, the resulting solids can be filtered off and worked up in a conventional manner to yield the desired R,R labetalol, HCl salt.

If desired, the acid addition salt i.e., either the dibenzoyl-d-tartrate or HCl salt can be further treated by conventional techniques to provide the free R,R-amine base.

EXAMPLE 1

A. Into a Paar hydrogenation bottle charge: 121.2 g (1.00 mole) of D-(+)-α-methylbenzylamine, 173.4 g (1.17 mole, 17% excess) of benzylacetone, 60.1 g (1.00 mole) of glacial acetic acid and 600 ml isopropanol. Add 80 g (wet weight) of Raney Nickel (Grace No. 28), washed with water to neutral and then with isopropanol to remove the water. Hydrogenate the mixture under 60 psi hydrogen pressure.

Filter the resulting mixture through a short bed of celite. Wash the catalyst and celite with 3×100 ml of isopropanol. Combine the isopropanol solutions and dilute with a further 660 ml of isopropanol. To this solution add, with efficient stirring over a period of about 30 minutes, 467 ml of a 2.25N (1.05 mole) solution of gas HCl in isopropanol. After about half of the HCl/isopropanol is added, the product starts precipitating. The temperature rises to 33° C. Cool to ambient temperature and stir for 3 hours. Filter the solid and wash on filter with 100 ml isopropanol. Dry the resulting solid at 50° C. to yield a white solid m.p. 216.5°–218° C., $[\alpha]_D^{26} = +59.6°$ (1% in MeOH).

Recrystallize the solid from isopropanol using 15 ml of solvent per gram of material. Cool to ambient temperature and stir for 3 hours. Filter and wash the solid on the filter with 2×100 ml isopropanol. Dry the solid at 50° C. to constant weight to obtain a white crystalline solid, m.p. 219°–220.5° C., $[\alpha]_D^{26} = +60.8°$ (1% in MeOH).

B. Charge 78.0 g (0.269 mole) of the R,R-amine-HCl salt, 390 ml toluene and 135 ml of a 3 molar aq. NaOH solution (0.405 mole, 50% excess) into a vessel and heat at 80° C. with stirring, under nitrogen for 1 hour. Separate the resulting layers. Extract the water layer with 80 ml toluene. Combine toluene extracts and wash with 2×80 ml saturated aq. NaHCO$_3$ (pH of last washing should be 9), with 2×80 ml water (last washing should be neutral) and 80 ml saturated aq. NaCl. Dry the toluene extracts with Na$_2$SO$_4$. Remove the solvent in vacuo. Distill the product at 128°–134°/0.9 mm Hg. A clear colorless liquid, 67.3 g (98.7% yield), $[\alpha]_D = +78.4°$ (neat) or $[\alpha]_D = +115.2°$ (10% in MeOH) is obtained.

C. In a 1 liter three necked flask equipped with stirrer, thermometer and reflux condenser charge 200 ml of dimethylformamide (dried over 4 A molecular sieves), 83.6 g (0.24 moles) of 2-(phenylmethoxy)-5-(bromomethylcarbonyl)benzamide, 50.7 g (0.2 moles) of the amine from Step 8 and 35 ml (29 g; 0.5 moles) of propylene oxide.

Heat the stirred suspension to 45°–47° C. and maintain the resulting solution at this temperature for 24 hours. The color or the solution changes from yellow to orange and later to reddish orange. Protect the reaction mixture from light at all times during the reaction and the subsequent work-up.

After 24 hours remove a sample and check the completion of the reaction. When the reaction is complete, cool the reaction mixture to room temperature and pour into a stirred mixture of 600 ml of water and 200 ml of CH$_2$Cl$_2$.

Separate the phases, extract the aqueous layer twice with 200 and 100 ml of CH$_2$Cl$_2$ and wash the combined organic layers with 3×200 ml of water. Dry thoroughly over anhydrous Na$_2$SO$_4$ or MgSO$_4$, filter, wash the cake with 2×5 ml of CH$_2$Cl$_2$ and remove the solvent under reduced pressure (120 mm Hg and water bath temperature of about 40° C.).

Dissolve the red, viscous residue in 500 ml of 2B ethanol and proceed immediately to the next step.

D. Cool the solution of amino-ketone obtained from Step C to 5° C.+2° C. under a blanket of nitrogen in a 2 liter three necked flask equipped with a mechanical stirrer and thermometer.

Add to the reaction mixture 7.6 g (0.2 moles) of NaBH$_4$ in portions such as to maintain the temperature and to avoid violet frothing of evolving H$_2$. After the addition is complete, maintain the reaction mixture at 5° C.+2° C. for an hour then let slowly warm to room temperature and continue to stir the mixture for 16–18 hours. Provide intermittent cooling to avoid temperatures higher than 25° C.

Check for completion of reduction by the absence of starting amino-ketone. After completion of the reaction, distill out about 350 ml of EtOH under reduced pressure—approximately 120 mm Hg—and up to a pot temperature of 40° C.

Add 500 ml of water and reflux the mixture for 1 hour (pot temperature about 86° C.), after which, distill off about 150 ml of EtOH at atmospheric pressure. Cool the reaction mixture to 40° C. and extract the yellow, soft resin that separates with 300 ml of CH$_2$Cl$_2$. Cool the two phase mixture to room temperature, separate and extract the aqueous layer with 125 ml of CH$_2$Cl$_2$. Wash the combined organic layers with 2×200 ml of water. Dry the solution over anhydrous Na$_2$SO$_4$ or MgSO$_4$, filter and wash the cake with 2×50 ml of CH$_2$Cl$_2$.

Remove solvent under reduced pressure. Dissolve the residue in 650 ml of EtOH. Add 12 g (11.5 ml, 0.2 moles) of acetic acid and 6.25 g of Darco G-60 (activated carbon, Atlas Powder Co., Wilmington, Del.), heat to 65° C. and stir for 10 minutes at 65° C. Filter hot through a celite bed, and wash the resulting cake with 3×150 ml of hot ethanol; the resulting ethanol solution being used in Step 5.

E. Charge the ethanolic solution obtained in Step D into a hydrogenation flask, cool the contents in an icebath and add, under a blanket of N$_2$ 10 g of 5% Pd/C. Allow the solution to warm to room temperature and reduce in a Parr apparatus with H$_2$ under about 60 psi pressure.

After the reduction is complete, filter the catalyst through a celite bed and wash the cake with 2×125 ml of ethanol.

Add to the filtrate a solution of 75.28 g (0.2 moles) of dibenzoyl-d-tartaric acid monohydrate in 200 ml of ethanol. Seed with good quality salt and stir the mixture at room temperature for 3 days. A fine white precipitate slowly forms.

Filter the precipitated salt, wash with 125 ml of icecold ethanol and dry in a draft oven at 50° C. A white power is obtained (m.p. 168°–170° C. to 173.5°–175° C., uncorrected).

Recrystallize the crude salt from 1400 ml of boiling 90% aqueous ethanol. After dissolution is complete, cool to room temperature, seed with the desired R,R DB-d-TA salt and stir the resulting suspension for 16–18 hours. Filter the precipitate, wash with 2×100 ml of 90% aqueous and dry in a draft oven at 50° C. 71.5–73 g of purified salt is obtained (m.p. 175°–176° C., uncorrected).

F. Into a three-neck round bottom flask equipped with a mechanical stirrer, thermometer, addition funnel and nitrogen bubbler charge: 6.87 g (0.01 mole) of pulverized DB-d-TA salt of the R,R stereoisomer obtained from Step E and 103 ml of isopropanol. Stir the mixture for about 30–45 minutes until a paste like, but very fluid and easily stirrable mixture is obtained. Add, in a fast stream, 4.8 ml of a 2.19N solution of HCl gas in ethanol (0.0105 mole; 5% excess). Stir the mixture efficiently, at ambient temperature, for about 6 hours. Filter the solid and wash on a filter with 3×12.5 ml of isopropanol. Dry in draft oven at 50° C. to constant weight to obtain the HCl salt of the R,R stereoisomer as a colorless solid, 3.43–3.46 g, m.p. 192°–193° C., rotation α=−15.3°; −15° ($D_MF$, C=1) diastereomeric purity: 98.9%, >99°.

I claim:

1. A method for the preparation of (−)-5-[(R)-1-hydroxy-2-((R)-1-methyl-3-phenylpropyl)aminoethyl]-salicylamide, which comprises:
   (1) reaction of N-((R)-α-methylbenzyl)-(R)-1-methyl-3-phenylpropylamine with a 4-O-protected-α-bromo-3-carbamoylacetophenone in the presence of a non-basic acid acceptor to produce a 2-(O-protected)-5-[(R)-α-methylbenzyl-N-((R)-1-methyl-3-phenylpropyl)glycyl]benzamide;
   (2) reduction of the glycyl carbonyl function in the product from Step (1) to hydroxy;
   (3) deprotection of the O and N functions of the product from Step (2);
   (4) resolution of the deprotected racemate from Step 3 by reaction with a suitable resolving agent to selectively precipitate the R,R stereoisomer as a salt thereof substantially free from the corresponding S,R stereoisomer.

2. A method according to claim 1, wherein the compound N-((R)-α-methylbenzyl)-(R)-1-methyl-3-phenylpropylamine is stereoselectively prepared by (a) reaction of D-(+)-α-methylbenzylamine with benzyl acetone in a reducing environment followed by (b) resolution of the diastereomeric mixture by selective precipitation and (c) generation of the free R,R amine.

3. A method according to claim 2, in which the resolution in step (b) is carried out by the formation and selective precipitation of the R,R amine HCl acid addition salt.

4. A method according to claim 1, in which the non-basic acid acceptor is propylene oxide.

5. A method according to claim 1, in which the resolution in step (4) is carried out using (−)-dibenzoyl-d-tartrate as the resolving agent.

6. 2-(O-benzyl)-5-[(R)-α-methylbenzyl-N-((R)-1-methyl-3-phenylpropyl)glycyl]benzamide.

7. 2-(O-benzyl)-5-[(R,S)-1-hydroxy-2-[((R)-1-methyl-3-phenylpropyl)-(R)-α-methylbenzylamino]ethyl]benzamide.

* * * * *